(12) United States Patent
Osabe et al.

(10) Patent No.: US 6,869,788 B2
(45) Date of Patent: Mar. 22, 2005

(54) DNA ENCODING NOVEL D-AMINOACYLASE AND PROCESS FOR PRODUCING D-AMINO ACID BY USING THE SAME

(75) Inventors: Masami Osabe, Mobara (JP); Katsuyuki Takahashi, Mobara (JP); Toshifumi Yamaki, Mobara (JP); Teruo Arii, Mobara (JP); Toshihiro Oikawa, Mobara (JP)

(73) Assignee: Mitsui Chemicals, Inc., Tokyo (JP)

( * ) Notice: Subject to any disclaimer, the term of this patent is extended or adjusted under 35 U.S.C. 154(b) by 110 days.

(21) Appl. No.: 10/240,422

(22) PCT Filed: Feb. 1, 2002

(86) PCT No.: PCT/JP02/00853

§ 371 (c)(1),
(2), (4) Date: Sep. 30, 2002

(87) PCT Pub. No.: WO02/061077

PCT Pub. Date: Aug. 8, 2002

(65) Prior Publication Data

US 2003/0207436 A1 Nov. 6, 2003

(30) Foreign Application Priority Data

Feb. 1, 2001 (JP) .......................... 2001-024986

(51) Int. Cl.$^7$ ............................ C12N 9/78; C12Q 1/34; C12P 13/22; C07K 17/00; C07H 21/04

(52) U.S. Cl. .......................... 435/227; 435/18; 435/108; 435/69.1; 435/320.1; 435/252.3; 435/106; 530/350; 536/23.2

(58) Field of Search .......................... 435/227, 18, 108, 435/320.1, 69.1, 252.3, 106; 536/23.2; 530/350

(56) References Cited

FOREIGN PATENT DOCUMENTS

WO   WO 00/23598 A1   4/2000
WO   WO 00/78926 A1   12/2000

OTHER PUBLICATIONS

Witkowski et al., Biochemistry 38:11643–11650, 1999.*
Broun et al., Science 282:1315–1317, 1998.*
Seffernick et al., J. Bacteriol. 183(8):2405–2410, 2001.*
Wakayama, M. et al., Cloning and Sequencing of a Gene Encoding D–Aminoacylase from *Alcaligenes xylosoxydans* subsp. *xylosoxydans* A–6 and Expression of the Gene in *Escherichia coli*, Biosci. Biotech. Biochem., 1995, vol. 59, no. 11, pp. 2115–2119.
Wakayama, M. et al., Cloning, Expression and Nucleotide Sequence of the N–Acyl–D–Aspartate Amidohydrolase Gene from *Alcaligenes xylosoxydans* subsp. *xylosoxydans* A–6, Journal of Fermentation and Bioengineering, 1995, vol. 80, No. 4, pp. 311–317.
Wakayama, M. et al., Primary Structure of N–Acyl–D–Glutamate Amidohydrolase from *Alcaligenes xylosoxydans* subsp. *xylosoxydans* A–6, J. Biochem., 1995, vol. 118, pps. 204–209.

* cited by examiner

*Primary Examiner*—Rebecca E. Prouty
*Assistant Examiner*—Delia M. Ramirez
(74) *Attorney, Agent, or Firm*—Burns, Doane, Swecker & Mathis, L.L.P.

(57) ABSTRACT

This invention provides a novel D-aminoacylase obtained by cloning a DNA encoding the novel D-aminoacylase from Methylobacterium mesophilicum MT 10894, etc. and which shows sufficiently high activity at an industrially useful substrate concentration to allow a D-amino acid to be efficiently produced from an N-acyl-DL-amino acid; a DNA encoding the D-aminoacylase; a process for producing a D-amino acid from the corresponding N-acylamino acid using a transformant containing the DNA.

9 Claims, 1 Drawing Sheet

SEQUENCE LISTING

<160> NUMBER OF SEQ ID NOS: 3

<210> SEQ ID NO 1
<211> LENGTH: 1464
<212> TYPE: DNA
<213> ORGANISM: Methylobacterium mesophilicum

<400> SEQUENCE: 1

```
atgaccgaca gcacccgtaa gcacgacctg atcatccgcg gcggcaccgt catcgacggc      60
cgccggacgc cccgcttccg cgccgatgtg gcggtgcgcg acggccgact gagcgccatc     120
ggcgatctgg cggaccatcg ggccgcccag gagatcgatg ccacgggacg catcgtggcg     180
ccgggcttca tcgactcgca cacgcacgat gaccaggcgg tgctgtcgca gccgcagatc     240
ccgttcaagg tgtcgcaggg cgtcacgacg gtgatcgccg gcaattgcgg catcagcgcg     300
gcgccgctgc ggcgggacat ggacctgccc atgcccctca acctgatcga cgtgcccgcc     360
gaggagcgct tcacccgctt cgccgactac ctggatgcgc tgcgtgcccg ccctcgtcg     420
gtcaacgtgg ccgcgatggt cggccactcc accctgcgcg ccgtcaccat gccggcgctg     480
gaccgcgagg ccaacagcga ggaaatcgca cgcatgcgcg cgctggtgca ggaggcgatg     540
gacgcgggcg ccatcggcgt ctccaccggc accttctatc cacccgcggt gaaggccacc     600
acggaggaga tcatcgaagt ctgccggccc ctcactgccg cggggggcct gtacgtcacc     660
cacatgcggg acgagtccga ccaggtgatg acctcgctgg aagagacctt ccgcatcggc     720
cgcgcgctgg acgtgccggt ggtcgtctcc caccacaaag tgcagaacac gcccaacttc     780
ggcaagtcgc aggtcacgct gcccttcatc cgcgaagcca tgcaacgcca gcgcgtgtgc     840
ctcgactgct atccctacac ggcgggctcg accatgatcc gcgcggaccg gggcatgctc     900
gaaggccgcg tgctgatcgc cgagagcctg ccgcatccgg aatgcgcagg ccgcgacctg     960
gacgacatcg cccgcgactg gggcgtggac cgggtggagg ccgcccgccg gctgcagccc    1020
ggcagcgcca tctacttcct gatggacgag ggcgatgtgc agcgcatcct ggccttcgac    1080
gacacgatga tcggctcgga cggcatcccg gtcggcagca agccgcatcc gcggctctgg    1140
ggcaccttcc cgcgcgtgct gggccattac agccgcgacg tcggcctgtt ccccctggag    1200
accgccgtct ggaagatgac cggactcacg gcccgcaact tcggcctgca cggccggggc    1260
acgctggagg ccggccaggc cgccgacatc gtggtcttcg atgccggcac cgtgcgcgac    1320
gcggccgact atgccgagcc cacgcgtccc gcggaaggca tcgatgcggt gatcgtcaat    1380
ggcgccatca cctggcaagg cggccagcac acgggcgcac gccagggtca ggtcatccgc    1440
cgccaggcgg ccccatccca ctga                                          1464
```

<210> SEQ ID NO 2
<211> LENGTH: 487
<212> TYPE: PRT
<213> ORGANISM: Methylobacterium mesophilicum

<400> SEQUENCE: 2

```
Met Thr Asp Ser Thr Arg Lys His Asp Leu Ile Ile Arg Gly Gly Thr
  1               5                  10                  15

Val Ile Asp Gly Arg Arg Thr Pro Arg Phe Arg Ala Asp Val Ala Val
             20                  25                  30

Arg Asp Gly Arg Leu Ser Ala Ile Gly Asp Leu Ala Asp His Arg Ala
         35                  40                  45
```

-continued

Ala Gln Glu Ile Asp Ala Thr Gly Arg Ile Val Ala Pro Gly Phe Ile
    50                  55                  60

Asp Ser His Thr His Asp Asp Gln Ala Val Leu Ser Gln Pro Gln Ile
65              70                  75                  80

Pro Phe Lys Val Ser Gln Gly Val Thr Val Ile Ala Gly Asn Cys
                85                  90                  95

Gly Ile Ser Ala Ala Pro Leu Arg Arg Asp Met Asp Leu Pro Met Pro
            100                 105                 110

Leu Asn Leu Ile Asp Val Pro Ala Glu Glu Arg Phe Thr Arg Phe Ala
        115                 120                 125

Asp Tyr Leu Asp Ala Leu Arg Ala Arg Pro Ser Ser Val Asn Val Ala
    130                 135                 140

Ala Met Val Gly His Ser Thr Leu Arg Ala Val Thr Met Pro Ala Leu
145                 150                 155                 160

Asp Arg Glu Ala Asn Ser Glu Glu Ile Ala Arg Met Arg Ala Leu Val
                165                 170                 175

Gln Glu Ala Met Asp Ala Gly Ala Ile Gly Val Ser Thr Gly Thr Phe
            180                 185                 190

Tyr Pro Pro Ala Val Lys Ala Thr Thr Glu Glu Ile Ile Glu Val Cys
        195                 200                 205

Arg Pro Leu Thr Ala Ala Gly Gly Leu Tyr Val Thr His Met Arg Asp
    210                 215                 220

Glu Ser Asp Gln Val Met Thr Ser Leu Glu Glu Thr Phe Arg Ile Gly
225                 230                 235                 240

Arg Ala Leu Asp Val Pro Val Val Ser His His Lys Val Gln Asn
                245                 250                 255

Thr Pro Asn Phe Gly Lys Ser Gln Val Thr Leu Pro Phe Ile Arg Glu
            260                 265                 270

Ala Met Gln Arg Gln Arg Val Cys Leu Asp Cys Tyr Pro Tyr Thr Ala
        275                 280                 285

Gly Ser Thr Met Ile Arg Ala Asp Arg Gly Met Leu Glu Gly Arg Val
    290                 295                 300

Leu Ile Ala Glu Ser Leu Pro His Pro Glu Cys Ala Gly Arg Asp Leu
305                 310                 315                 320

Asp Asp Ile Ala Arg Asp Trp Gly Val Asp Arg Val Glu Ala Ala Arg
                325                 330                 335

Arg Leu Gln Pro Gly Ser Ala Ile Tyr Phe Leu Met Asp Glu Gly Asp
            340                 345                 350

Val Gln Arg Ile Leu Ala Phe Asp Asp Thr Met Ile Gly Ser Asp Gly
        355                 360                 365

Ile Pro Val Gly Ser Lys Pro His Pro Arg Leu Trp Gly Thr Phe Pro
    370                 375                 380

Arg Val Leu Gly His Tyr Ser Arg Asp Val Gly Leu Phe Pro Leu Glu
385                 390                 395                 400

Thr Ala Val Trp Lys Met Thr Gly Leu Thr Ala Arg Asn Phe Gly Leu
                405                 410                 415

His Gly Arg Gly Thr Leu Glu Ala Gly Gln Ala Ala Asp Ile Val Val
            420                 425                 430

Phe Asp Ala Gly Thr Val Arg Asp Ala Asp Tyr Ala Glu Pro Thr
        435                 440                 445

Arg Pro Ala Glu Gly Ile Asp Ala Val Ile Val Asn Gly Ala Ile Thr
    450                 455                 460

Trp Gln Gly Gly Gln His Thr Gly Ala Arg Gln Gly Gln Val Ile Arg

```
465                 470             475             480
Arg Gln Ala Ala Pro Ser His
                485

<210> SEQ ID NO 3
<211> LENGTH: 5
<212> TYPE: PRT
<213> ORGANISM: Methylobacterium mesophilicum

<400> SEQUENCE: 3

Thr Asp Ser Thr Arg
 1               5
```

DNA ENCODING NOVEL D-AMINOACYLASE AND PROCESS FOR PRODUCING D-AMINO ACID BY USING THE SAME

TECHNICAL FIELD

This invention relates to a novel D-aminoacylase exhibiting high activity at an industrially effective substrate concentration and particularly allowing D-tryptophan to be stereoselectively and effectively produced from N-acetyl-DL-tryptophan, and a process for producing a D-amino acid from an N-acylamino acid using it. This invention also relates to a base sequence encoding the D-aminoacylase, a plasmid containing it and a transformant produced by transformation by the plasmid. This invention also relates to a process for producing a D-aminoacylase using the transformant. This invention also relates to a process for producing a corresponding optically active D-amino acid from an N-acylamino acid by the action of the D-aminoacylase in the form of the transformant, its culture or its processed product on an N-acylamino acid.

BACKGROUND ART

D-amino acids are important as intermediates for a variety of pesticides, antibiotics and medicinal drugs. Many studies have been studied for their synthesis. To date, a DL-amino acid can be resolved by a physiochemical, chemical or enzymatic method, among which an enzymatic method has been considered to be most convenient and advantageous. In a known example of an enzymatic method, an N-acetyl-DL-amino acid is hydrolyzed using a D-aminoacylase to directly produce a corresponding D-amino acid.

Known sources of D-aminoacylases include microorganism belonging to bacteria, actinomyces and mold such as Pseudomonas (Japanese Patent Publication (JP-B) No. 60-31477), Streptomyses (JP-B 53-36035), Alcaligenes (JP-B 07-83711), Rhodococcus, Pimelobacter (Japanese Patent Laid-Open (JP-A) No. 06-227789), Arthrobacter, Corynebacterium, Erwinia, Escherichia, Flavobacterium, Norcadia, Protaminobacter, Xanthomonas (Japanese Patent Laid-Open (JP-A) No. 11-113592), Amycolatopsis (JP-A 11-98982), Sebekia (JP-A 11-318442), Hypomyces, Fusarium, Auricularia, Pythium, Menisporosis (JP-A 12-41684). There has been reported production of a D-amino acid using the action of a D-aminoacylase derived from any of these sources on an N-acylamino acid.

These D-aminoacylases, however, exhibit insufficient activity at a useful substrate concentration, and thus an industrially available D-aminoacylase has been needed. In particular, in hydrolysis of N-acetyl-D-tryptophan, these enzymes exhibit inadequate activity at a useful concentration. They cannot be, therefore, called industrially satisfactory enzymes. Recently, Tokuyama (JP-A 13-275688) and Taylor (Chirotech Technology Limited, WO 00/23598) have disclosed, as a D-aminoacylase which acts on N-acetyl-D-tryptophan to produce D-tryptophan, D-aminoacylases derived from Hypomyces and from Alcaligenes, respectively. Either of these D-aminoacylases which can hydrolyze N-acetyl-D-tryptophan only up to 10 g/L, cannot be regarded to be an enzyme which can catalyze the reaction at a useful concentration.

D-amino acids are important as starting materials for medical drugs, and thus there have been needed to develop a process for production thereof at a lower cost. There have been known no D-aminoacylases which can effectively catalyze a D-amino acid.

DISCLOSURE OF THE INVENTION

An objective of this invention is to provide a novel D-aminoacylase exhibiting efficiently high activity at an industrially useful substrate concentration and allowing a D-amino acid to be efficiently produced from an N-acetyl-DL-amino acid, and a process for producing a D-amino acid from an N-acylamino acid using it. Another objective of this invention is to provide a base sequence encoding the D-aminoacylase as a useful material for producing the D-aminoacylase and producing the D-amino acid using the D-aminoacylase; a plasmid containing the base sequence; and a transformant produced by transformation of a host by the plasmid.

While attempting to solve the problems, we have evaluated the properties of D-aminoacylases derived from a variety of microorganisms. In the study of relationship between a substrate concentration and a reaction rate, we have surprisingly found that, in a known D-aminoacylase, a higher substrate concentration more significantly reduces its reaction rate, i.e., inhibition of enzyme activity. Such phenomenon is particularly remarkable when a substrate is N-acetyl-D-tryptophan. We have assumed that in a conventional D-aminoacylase, such a phenomenon may cause production of D-tryptophan from N-acetyl-DL-tryptophan to be ineffective at a useful substrate concentration.

Thus, we have searched a novel D-aminoacylase exhibiting higher activity even at a higher substrate concentration without inhibition in N-acetyl-D-tryptophan, while testing a variety of microorganisms, and have finally found microorganism exhibiting novel D-aminoacylase activity meeting the above objective, belonging to Methylobacterium and Nocardioides. By combining various purification methods, we have successively sequenced a D-aminoacylase derived from the microorganism belonging to Methylobacterium to give the sequence with an N-terminal amino acid residue of SEQ. ID. No. 3. We have further obtained a DNA having the sequence of SEQ. ID. No. 1. in the Sequence Table; have produced a transformant from a plasmid containing a DNA fragment having the sequence; have produced the D-aminoacylase as an activated form; and have highly effectively produced a corresponding D-amino acid from an N-acylamino acid at a useful substrate concentration. We have thus achieved this invention.

This invention which we have achieved on the basis of the above new observation encompasses the following aspects.

(1) A D-aminoacylase capable of catalyzing a reaction forming a corresponding D-amino acid by acting on an N-acyl-D-amino acid,
  wherein in catalyzing a reaction forming D-tryptophan from N-acetyl-D-tryptophan in an aqueous medium, a reaction rate at an N-acetyl-D-tryptophan concentration of 50 g/L is at least 40% of a reaction rate at an N-acetyl-D-tryptophan concentration of 5 g/L.

(2) The D-aminoacylase as described in (1) wherein a reaction rate at an N-acetyl-D-tryptophan concentration of 100 g/L is at least 20% of a reaction rate at an N-acetyl-D-tryptophan concentration of 5 g/L.

(3) The D-aminoacylase as described in (1) derived from a microorganism belonging to Methylobacterium or Nocardioides.

(4) The D-aminoacylase as described in (3) wherein the microorganism belonging to Methylobacterium is Methylobacterium mesophilicum and the microorganism belonging to Nocardioides is Nocardioides thermolilacinus.

(5) The D-aminoacylase as described in (4) wherein the microorganism belonging to Nocardioides thermolilacinus is Nocardioides thermolilacinus ATCC 35863 strain.

(6) A D-aminoacylase capable of catalyzing a reaction forming a D-amino acid by acting on an N-acyl-D-amino acid, comprising:
(A) the amino acid sequence of SEQ. ID. No. 2 in the Sequence Table, or
(B) a variant amino acid sequence formed by insertion, deletion or substitution of at least one amino acid residue in the above amino acid sequence with the catalyst activity being maintained.

(7) The D-aminoacylase as described in (6) wherein in catalyzing a reaction forming D-tryptophan from N-acetyl-D-tryptophan in an aqueous medium, a reaction rate at an N-acetyl-D-tryptophan concentration of 50 g/L is at least 40% of a reaction rate at an N-acetyl-D-tryptophan concentration of 5 g/L.

(8) The D-aminoacylase as described in (7) wherein a reaction rate at an N-acetyl-D-tryptophan concentration of 100 g/L is at least 20% of a reaction rate at an N-acetyl-D-tryptophan concentration of 5 g/L.

(9) A base sequence encoding a D-aminoacylase capable of catalyzing a reaction forming a D-amino acid by acting on an N-acyl-D-amino acid, consisting of:
(a) the base sequence of SEQ. ID. No. 1 in the Sequence Table, or
(b) a variant base sequence formed by insertion, deletion or substitution of at least one base in the base sequence of SEQ. ID. No. 1 with the D-aminoacylase activity encoded in the above base sequence being maintained.

(10) The base sequence as described in (9) wherein the variant base sequence hybridizes with the base sequence of SEQ. ID. No. 1 under stringent conditions.

(11) The base sequence as described in (9) wherein in catalyzing a reaction forming D-tryptophan from N-acetyl-D-tryptophan in an aqueous medium, a reaction rate at an N-acetyl-D-tryptophan concentration of 50 g/L is at least 40% of a reaction rate at an N-acetyl-D-tryptophan concentration of 5 g/L.

(12) The base sequence as described in (11) wherein a reaction rate at an N-acetyl-D-tryptophan concentration of 100 g/L is at least 20% of a reaction rate at an N-acetyl-D-tryptophan concentration of 5 g/L.

(13) A plasmid comprising the base sequence as described in (9).

(14) A transformant produced from transformation by the plasmid as described in (13).

(15) A process for producing a D-aminoacylase comprising the step of culturing the transformant as described in (14) to form the D-aminoacylase encoded by the base sequence in the plasmid incorporated into the transformant.

(16) A process for producing an optically active amino acid comprising the step of producing a corresponding D-amino acid by the action of a D-aminoacylase on an N-acylamino acid in an aqueous medium, wherein in catalyzing a reaction forming D-tryptophan from N-acetyl-D-tryptophan by the D-aminoacylase in an aqueous medium, a reaction rate at an N-acetyl-D-tryptophan concentration of 50 g/L is at least 40% of a reaction rate at an N-acetyl-D-tryptophan concentration of 5 g/L.

(17) The process as described in (16) wherein a reaction rate at an N-acetyl-D-tryptophan concentration of 100 g/L is at least 20% of a reaction rate at an N-acetyl-D-tryptophan concentration of 5 g/L.

(18) The process as described in (16) wherein the aminoacylase is derived from a microorganism belonging to Methylobacterium or Nocardioides.

(19) The process as described in (18) wherein the microorganism belonging to Methylobacterium is Methylobacterium mesophilicum and the microorganism belonging to Nocardioides is Nocardioides thermolilacinus.

(20) The process as described in (19) wherein the microorganism belonging to Nocardioides thermolilacinus is Nocardioides thermolilacinus ATCC 35863 strain.

(21) The process as described in (16) wherein a concentration of the N-acylamino acid is 50 g/L or more.

(22) The process as described in (21) wherein a concentration of the N-acylamino acid is 100 g/L or more.

(23) A process for producing an optically active amino acid comprising the step of producing a corresponding D-amino acid by the action of a D-aminoacylase on an N-acylamino acid in an aqueous medium, wherein the D-aminoacylase is the D-aminoacylase as described in (6).

(24) The process as described in (23) wherein in catalyzing a reaction forming D-tryptophan from N-acetyl-D-tryptophan by the D-aminoacylase in an aqueous medium, a reaction rate at an N-acetyl-D-tryptophan concentration of 50 g/L is at least 40% of a reaction rate at an N-acetyl-D-tryptophan concentration of 5 g/L.

(25) The process as described in (24) wherein a reaction rate at an N-acetyl-D-tryptophan concentration of 100 g/L is at least 20% of a reaction rate at an N-acetyl-D-tryptophan concentration of 5 g/L.

(26) The process as described in (23) wherein the N-acylamino acid is subject to the action of the D-aminoacylase in the form of a culture obtained by culturing the transformant as described in (14), a transformant separated from the culture or a processed material thereof.

(27) The process as described in (23) wherein a concentration of the N-acylamino acid is 50 g/L or more.

(28) The process as described in (27) wherein a concentration of the N-acylamino acid is 100 g/L or more.

A D-aminoacylase according to this invention can be used to produce a corresponding D-amino acid from an N-acylamino acid at an improved reaction rate at an industrially useful substrate concentration. This invention can also provide a base sequence useful in production using a gene recombination technique of the useful D-aminoacylase, a plasmid containing the sequence and a transformant produced by transforming a host by the plasmid.

BEST MODE FOR CARRYING OUT THE INVENTION

Figure 1:
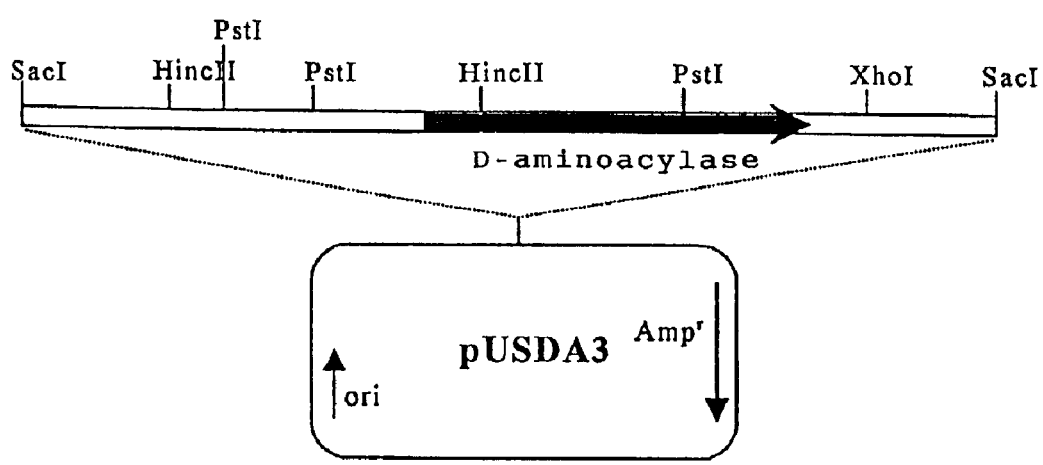
FIG. 1 shows a physical map of a recombinant plasmid pUSDA3. In the figure, "ori" and "Ampr'" indicate a replication origin of the plasmid and an ampicillin resistance marker, respectively; "SacI", "HincII", "PstI" and "XhoI" indicate restriction sites; and the bold arrow indicates the position and the direction of an ORF in the D-aminoacylase.

A D-aminoacylase according to this invention is an enzyme capable of catalyzing a reaction for production of a corresponding D-amino acid by acting on an N-acyl-D-amino acid. In particular, it little exhibits inhibition for N-acetyl-D-tryptophan and exhibits higher activity even at a higher substrate concentration. The inhibition by N-acetyl-D-tryptophan can be defined by the following relationship between a substrate concentration and a reaction rate.

I. In an aqueous medium, a reaction rate at an N-acetyl-D-tryptophan concentration of 50 g/L is at least 40% of a reaction rate at an N-acetyl-D-tryptophan concentration of 5 g/L.

II. A reaction rate at an N-acetyl-D-tryptophan concentration of 100 g/L is at least 20% of a reaction rate at an N-acetyl-D-tryptophan concentration of 5 g/L.

A D-aminoacylase according to this invention has property I described above, preferably both properties I and II. This invention shall, therefore, encompass a D-aminoacylase derived from any microorganism or even any known D-aminoacylase modified by gene recombination as long as it exhibits at least the D-aminoacylase activity described in inhibition property I.

It is more preferable in terms of property I that a reaction rate at an N-acetyl-D-tryptophan concentration of 50 g/L is at least 50%, particularly at least 60% of a reaction rate at an N-acetyl-D-tryptophan concentration of 5 g/L. In terms of property II, it is more preferable that a reaction rate at an N-acetyl-D-tryptophan concentration of 100 g/L is at least 25%, particularly at least 30% of a reaction rate at an N-acetyl-D-tryptophan concentration of 5 g/L.

A relationship between a substrate concentration and a reaction rate in this invention can be determined as follows. For example, 200 μL of an enzyme solution having an adequate activity to a reaction is added to 200 μL of a 100 mM phosphate buffer containing 10, 50, 100 or 200 g/L of a substrate (N-acetyl-D-tryptophan), and the mixture is allowed to react at 30° C. for an appropriate time. The amount of D-tryptophan by the reaction can be determined by, e.g., HPLC for comparing an enzyme activity (reaction rate) at each substrate concentration. There are no restrictions to an aqueous medium used in determining a reaction rate in this invention as long as it allows the enzyme reaction to proceed; for example, water as well as a buffer prepared by adding to water one or more ingredients appropriately selected from the group consisting of phosphoric acid, Tris, citric acid, acetic acid, boric acid, glycine, HEPES, MOPS, MES, CAPS, CHES and PIPES. A reaction temperature can be selected from the temperature range including an optimal temperature. For example, it is particularly preferably maintained at 30 to 60° C. A reaction pH may be also within a range that the D-aminoacylase can maintain its activity, particularly pH 6 to 11 including an optimal pH. The enzyme can be a microbe culture itself, microbe obtained by separation and collection using centrifugation, or an extract, a ground product or a purified product from the microbe. Conditions such as the amount of an enzyme and a reaction time during determining a reaction rate in this invention may be those under which a reaction rate can be properly determined; for example, those under which a reaction does not reach saturation during a time for determining the reaction rate, preferably those where an accumulated concentration of D-tryptophan produced is about 0.2 g/L to 1 g/L when a concentration of N-acetyl-D-tryptophan as a substrate is 5 g/L.

The physical properties of the D-aminoacylase according to this invention are as follows:

| | |
|---|---|
| Optimal pH: | pH 8 to 10 (most preferably pH 9); |
| Optimal temperature: | 60° C.; |
| Thermal stability: | 80% remaining activity after heating at 40° C. for 20 hours. |

An aspect of the D-aminoacylase according to this invention has the amino acid sequence of SEQ. ID. No. 2 in the Sequence Table, or an amino acid sequence obtained by substitution, deletion, modification or insertion of one or two, preferably several amno acids to the amino acid sequence of SEQ. ID. No. 2 with the D-aminoacylase activity being maintained.

A polynucleotide encoding the D-aminoacylase according to this invention comprises the base sequence of SEQ. ID. No. 1 in the Sequence Table. The base sequence of SEQ. ID. No. 1 encodes the protein of SEQ. ID. No. 2, although the base sequence encoding the amino acid sequence of SEQ. ID. No. 2 may be not limited to the base sequence of SEQ. ID. No. 1, but any base sequence based on a different codon. Furthermore, substitution, deletion, modification, insertion and/or addition may be appropriately introduced to provide a homologue of the polynucleotide. A homologue of the polynucleotide according to this invention may be produced by substitution, deletion or addition of a base (bases) to the base sequence of SEQ. ID. No. 1 within the range that a given enzyme activity can be maintained. An example of such a homologue is a polynucleotide having a base sequence capable of hybridizing with a polynucleotide having a complementary sequence of SEQ. ID. No. 1 under stringent conditions.

The hybridization under stringent conditions can be conducted as described in Molecular Cloning: Cold Spring Harbor Laboratory Press, Current Protocols in Molecular Biology; Wiley Interscience. An example of a commercially available system is the GeneImage system (Amersham). Specifically, the hybridization can be conducted by the following procedure. A film on which DNA or RNA molecules to be tested have been transcribed is hybridized with a labeled probe in a hybridization buffer indicated in the product protocol in accordance with the protocol. A composition of the hybridization buffer is 0.1 wt % SDS, 5 wt % dextran sulfate, a 1/20 dilution blocking reagent contained in the kit and 2 to 7×SSC. The blocking reagent may be, for example, prepared by diluting to 1/20 a 5-fold concentrate of 100×Denhardt's solution, 2% (weight/volume) bovine serum albumin, 2% (weight/volume) Ficll™ 400 and 2% (weight/volume) polyvinylpyrrolidone. 20×SSC is a solution of 3M sodium chloride and 0.3 M citric acid. SSC is used more preferably at 3 to 6×SSC, further preferably 4 to 5×SSC. A hybridization temperature is 40 to 80° C., more preferably 50 to 70° C., further preferably 55 to 65° C. After incubation for several hours or overnight, the film is washed with a washing buffer. A washing temperature is preferably room temperature, more preferably a hybridization temperature. A composition of the washing buffer is 6×SSC+0.1 wt % SDS solution, more preferably 4×SSC+0.1 wt % SDS solution, further preferably 1×SSC+0.1 wt % SDS solution, most preferably 0.1×SSC+0.1 wt % SDS solution. After washing the film with such a washing buffer, DNA or RNA molecules in which the probe has been hybridized can be identified utilizing the label in the probe.

Novel D-aminoacylase according to this invention include those derived from Methylobacterium mesophilicum MT 10894 strain and from Nocardioides thermolilacinus ATCC 35863 strain. The Methylobacterium mesophilicum MT 10894 strain has been isolated from a soil in Mobara-City, Ciba, Japan. Table 1 shows its bacteriological properties.

TABLE 1

| | |
|---|---|
| Culturing temperature | 30° C. |
| Cell morphology | bacillus (0.8 × 1.5 μm) |
| Gram staining | − |
| Spore | − |
| Motility | + |
| Colony morphology | Circular |
| | Entirely smooth |
| | Convex |
| | Gloss |
| | Pale yellow |
| Catalase | + |

TABLE 1-continued

| | | |
|---|---|---|
| Oxidase | | + |
| O/F test | | No fermentative decomposition |
| Nitrate reduction | | − |
| Indole production | | − |
| Dextrose acidification | | − |
| Arginine dihydrorase | | − |
| Urease | | + |
| Esculin hydrolysis | | − |
| Gelatin hydrolysis | | − |
| β-Galactosidase | | − |
| Growth on MacConkey agar | | − |
| Growth at 42° C. | | − |
| Ability of Utilizing Substrate | Glucose | + |
| | L-arabinose | + |
| | D-mannose | − |
| | D-mannitol | − |
| | N-acetyl-D-glucosamine | − |
| | Maltose | − |
| | Potassium gluconate | + |
| | n-Capric acid | − |
| | Adipic acid | − |
| | dl-Malic acid | + |
| | Sodium citrate | − |
| | Phenyl acetate | − |

The above bacteriological properties were compared with those in the categories described in Bergey's Manual of Systematic Bacteriology Vol. 1 (1984) William & Wilkins, Bergey's Manual of Determinative Bacteriology Ninth Edition (1994) Williams & Wilkins, G. I. Barrow and R. K. A. Feltham ed., Cowan & Steel's Manual for the Identification of Medical Bacteria 3rd. ed, Cambridge univ. press, (1993), to identify this strain. Thus, the strain is considered to belong to Methylobacterium mesophilicum. The strain MT 10894 was deposited to the National Institute Bioscience and Human-Technology of the National Institute of Advanced Industrial Science and Technology in the Ministry of Economy and Industry, (1-1-1, Higashi, Tsukuba, Ibaragi, Japan) as a deposition number FERM P-17771 on Mar. 8, 2000, which was changed to FERM BP-7856 after transfer to International deposition in accordance with Budapest treaty dated Jan. 21, 2002.

A DNA encoding a novel D-aminoacylase according to this invention can be isolated, for example, by the following procedure. A genome DNA is purified from a microorganism. After digesting with a restriction enzyme, the resulting DNAs are fractionated by their length by ultracentrifugation or electrophoresis. DNAs in the fractions are collected and incorporated into plasmids to provide a plasmid library. From the library, a clone exhibiting D-aminoacylase activity is selected to give a plasmid containing a DNA encoding a D-aminoacylase gene. The base sequence of the plasmid can be analyzed to determine the base sequence of a DNA encoding the desired D-aminoacylase gene and to deduce the amino acid sequence of the encoded D-aminoacylase from the base sequence of the DNA.

The DNA encoding the D-aminoacylase of this invention thus isolated can be incorporated into an expression plasmid, typically pUC18, pKK223-3, pBR322, Bluescript II SK(+) and pSC101 when a host is E. coli, to give a D-aminoacylase expression plasmid. Any organism may be used as a host for transformation as long as a recombinant vector can stably and autonomously grow and a trait of a foreign DNA can be expressed; for example, but not limited to, E. coli.

In this invention, a transformant obtained from transformation by the plasmid can be grown on the basis of known information and be allowed to produce the D-aminoacylase of this invention. Any artificial or natural medium may be used as long as it contains a carbon source, a nitrogen source, inorganics and other nutrients in proper amounts. Culturing can be conducted by a common culturing process such as shaking culture, aeration-spinner culture, continuous culture and feeding culture in a liquid medium containing the above culturing ingredients. Culturing conditions may be appropriately selected depending on various factors such as the type of culturing and a culturing method, and there are no restrictions as long as a host strain can produce the D-aminoacylase.

In a process for producing a D-amino acid according to this invention, a D-aminoacylase can be utilized as a culture itself of the above D-aminoacylase producing bacteria, transformant cells obtained by separation and collection using centrifugation of the culture or a processed bacterial product of the transformant. The term "processed bacterial product" as used herein refers to an extract or ground product from the transformant, a separation product obtained by separation and/or purification of D-aminoacylase active fractions in the extract or the ground product, or an immobilization product prepared by immobilizing the transformant or an extract, a ground product or a separation product from the transformant. An active component derived from a host organism may adversely affect the culture medium itself, a transformant obtained by separation and collection using centrifugation from the culture medium and/or reactivity or selectivity in a desired reaction of the processed bacterial product of the transformant. In such a case, the culture medium itself, the transformant obtained by separation and collection using centrifugation from the culture medium or the processed bacterial product of the transformant may be treated with an organic solvent or heated before or during the reaction, to improve reactivity and/or selectivity. The organic solvent may be appropriately one or more selected from alcohols such as methanol and ethanol; water-miscible organic solvents such as acetone, THF, DMF, DMI and DMSO; aromatic organic solvents such as toluene and benzene; esters such as ethyl acetate and butyl acetate; hydrocarbons such as hexane and heptane; halogenated hydrocarbons such as dichloromethane and chloroform; ethers such as diethyl ether. The amount of the organic solvent may be selected within a range where D-aminoacylase activity is stable. Heating may be conducted at about 40° C. to 70° C., desirably 45° C. to 55° C. in the light of stability of the D-aminoacylase. A heating period may be within a range where D-aminoacylase activity is stable; 30 to 100 min is adequate.

In treating an N-acyl-D-amino acid with the D-aminoacylase of this invention, it is desirable to select preferable conditions for reactivity such as activity and stability of the D-aminoacylase.

A medium used in the reaction may be water or an aqueous medium consisting of a variety of buffers. The buffer may be a buffer prepared by adding to water one or more ingredients appropriately selected from phosphoric acid, Tris, citric acid, acetic acid, boric acid, glycine, HEPES, MOPS, MES, CAPS, CHES, PIPES and others.

A variety of additives may be, if necessary, added for further improving a reaction efficiency or product yield. Some D-aminoacylases are activated with a metal ion such as $Zn^{2+}$ and $Co^{2+}$, and therefore, these bivalent metal ions can be added to a reaction. On the contrary, if the enzyme is inhibited by a metal ion, a chelating agent such as EDTA may be added.

A starting material used for preparing a D-amino acid in this invention (N-acylamino acid) contains an N-acyl-D- amino-acid which may be in the form of a DL-amino acid, an optically active amino acid enriched with the D-isomer or the pure D-isomer.

A concentration of the starting material is generally, but not limited to, about 1 g/L to 300 g/L. Particularly, in the light of reactivity and an economical efficiency, the concentration is preferably 50 g/L or more, more preferably 100 g/L or more and preferably 200 g/L or less. A reaction temperature is preferably maintained within a range where the D-aminoacylase can express its activity, particularly 30 to 60° C. A reaction pH is also preferably maintain within a range where the D-aminoacylase can express its activity, particularly pH 6 to 11.

A novel D-aminoacylase of this invention can provide corresponding D-amino acids from D-isomers of a variety of N-acylamino acids. Thus, the D-aminoacylase of this invention may be used to industrially advantageously prepare an optically amino acid from an N-acyl-DL-amino acid. An applicable N-acyl-DL-amino acid may be selected a wide range of compounds without limitations. Examples of a typical and preferable N-acyl-DL-amino acid include N-acyl-DL-methionine, N-acyl-DL-leucine, N-acyl-DL-tryptophan, N-acyl-DL-5-hydroxytryptophan, N-acyl-DL-phenylalanine, N-acyl-DL-phenylglycine, N-acyl-DL-homophenylalanine, N-acyl-DL-bishomophenylalanine, N-acyl-DL-p-nitrophenylalanine, N-acyl-DL-p-fluorophenylalanine, N-acyl-DL-p-chlorophenylalanine, N-acyl-DL-p-bromophenylalanine, N-acyl-DL-p-methoxyphenylalanine, N-acyl-DL-tyrosine, N-acyl-DL-p-cyanophenylalanine, N-acyl-DL-2-pyridylalanine, N-acyl-DL-3-pyridylalanine, N-acyl-DL-4-pyridylalanine, N-acyl-DL-o-benzylserine, N-acyl-DL-S-phenylcysteine, N-acyl-DL-1-naphthylalanine and N-acyl-DL-2-naphthylalanine. A further preferable N-acyl-DL-amino acid is an N-acetyl-DL-amino acid. In particular, substrate specificity to N-acetyl-D-phenylalanine or N-acetyl-D-tryptophan is particularly higher.

EXAMPLES

This invention will be more specifically described with reference to, but not limited to, examples.

Reactivity and an optical purity were evaluated by analyzing a D-amino acid produced in a reaction and a remaining N-acylamino acid by high performance liquid chromatography (column: CROWNPAK CR(−); Daicel Chemical Industries, Ltd.); column temperature: 40° C.; mobile phase: $HClO_4$ aq. pH 1.5 and 0 to 15% methanol (v/v); flow rate 0.8 mL/min, detection: 210 nm).

Example 1

Culturing of Methylobacterium Mesophilicum MT 10894 (FERM BP-7856)

To a liquid medium having the composition below was inoculated the bacteria grown on a broth agar plate, and the medium was shaken at 30° C. for 40 hours to prepare the bacteria exhibiting D-aminoacylase activity.

| Culture medium composition | |
|---|---|
| N-acetyl-DL-leucine: | 5 g/L |
| Glucose: | 10 g/L |
| Peptone: | 10 g/L |
| Potassium dihydrogen phosphate: | 1 g/L |
| Potassium hydrogenphosphate monobasic: | 1 g/L |
| Magnesium sulfate heptahydrate: | 0.1 g/L |
| Yeast extract: | 0.5 g/L |
| pH 7.0 (adjusted with KOH) | |

Example 2

Culturing of Nocardioides Thermolilacinus (ATCC 35863)

To a liquid medium having the composition below was inoculated the bacteria grown on a broth agar plate, and the medium was shaken at 30° C. for 100 hours to prepare the bacteria exhibiting D-aminoacylase activity.

| Culture medium composition | |
|---|---|
| N-acetyl-DL-leucine: | 5 g/L |
| Czapek-Dox Liquid medium modified (Oxoid): | 5 g/L |
| Yeast extract: | 2 g/L |
| Vitamin assay casamino acid: | 10 g/L |
| pH 7.2 (adjusted with KOH) | |

Example 3

Relationship Between a Substrate Concentration and a Reaction Rate in D-Aminoacylases Derived From Methylobacterium Mesophilicum MT 10894 (FERM BP-7856) and From Nocardioides Thermolilacinus (ATCC 35863) Crude Enzyme Solution A bacterial cell suspension (0.1 g/0.1 M phosphate buffer (pH 7.8) 1 mL) was prepared using each of Methylobacterium mesophilicum MT 10894 (FERM BP-7856) and Nocardioides thermolilacinus (ATCC 35863) obtained in Examples 1 and 2. Each suspension was homogenized by an ultrasonic homogenizer and the bacterial debris was precipitated by a refrigerated centrifuge. The supernatant was collected as a crude enzyme solution.

Substrate Solution

A substrate solution was prepared by dissolving N-acetyl-D-tryptophan in a 0.1 M phosphate buffer (pH 7.8) to a concentration of 200 g/L.

Determination

The substrate solution was diluted by volume with a 0.1 M phosphate buffer (pH 7.8) to prepare 200 μL of 5, 25, 50 and 100 g/L substrate solutions. After adding 200 μL of the crude enzyme solution, the mixture was reacted at 30° C. for 1 hour. Then, the reaction was quenched by adding 0.4 mL of a 1M phosphate buffer. Then, 0.4 mL of 1N sodium hydroxide was added to dissolve the precipitated unreacted acetyl compound. After removing the bacterial debris by centrifugation, D-tryptophan produced in the reaction solution was determined by HPLC. Table 2 shows relative D-tryptophan-forming rates by D-aminoacylases derived from different bacterial strains at substrate concentrations of 25, 50 and 100 g/L, assuming that a reaction rate at a substrate concentration of 5 g/L is 100.

TABLE 2

| N-acetyl-D-tryptophan concentration (g/L) | Methylobacterium mesophilicum (FERM BP-17771) | Nocardioides thermolilacinus (ATCC 35863) |
|---|---|---|
| 5 | 100 | 100 |
| 25 | 122 | 110 |
| 50 | 91 | 108 |
| 100 | 42 | 103 |

Comparative Example 1
Relationship Between a Substrate Concentration and a Reaction Rate in Known Bacterial Strains We have investigated relationship between a substrate concentration and a reaction rate in D-aminoacylases derived from known D-aminoacylase carrying bacterial strains, Alcaligenes denitrificans subsp. xylosodans MI4 (FERM P-9413) and Streptomyces tuirus (IFO 13418). Preparation methods for these strains will be described below. Alcaligenes denitrificans subsp. xylosodans MI4 (FERM P-9413) was prepared as described in Example 1. Streptomyces tuirus (IFO 13418) was prepared by culturing it in a liquid medium having the following composition at 30° C. for 48 hours.

| Culture medium composition | |
|---|---|
| D-valine: | 4 g/L |
| Glucose: | 10 g/L |
| Peptone: | 10 g/L |
| Potassium dihydrogen phosphate: | 1 g/L |
| Potassium hydrogenphosphate monobasic: | 1 g/L |
| Magnesium sulfate heptahydrate: | 0.5 g/L |
| Yeast extract: | 10 g/L |
| Cobalt chloride: | 1 mg/mL |
| pH 7.0 (adjusted with KOH) | |

Preparation of a crude enzyme solution and a substrate solution and determination of an enzyme activity were as described in Example 3. Table 3 shows relative D-tryptophan-forming rates by D-aminoacylases derived from different bacterial strains at substrate concentrations of 25, 50 and 100 g/L, assuming that a reaction rate at a substrate concentration of 5 g/L is 100.

TABLE 3

| N-acetyl-D-tryptophan concentration (g/L) | Alcaligenes denitrificans subsp. xylosodans MI4 (FERM P-9413) | Streptomyces tuirus (IFO 13418) |
|---|---|---|
| 5 | 100 | 100 |
| 25 | 36 | 45 |
| 50 | 13 | 22 |
| 100 | 4 | 6 |

Example 4
Sequencing of an N-terminal Amino Acid in a D-Aminoacylase Derived From Methylobacterium Mesophilicum MT 10894 (FERM P-17771)

The Methylobacterium mesophilicum was cultured and harvested as described in Example 1. The bacterial cells were suspended in a 0.1 M phosphate buffer (pH 7.8) containing 1 mM DTT (dithiothreitol). The bacterial cells in the suspension were homogenized by an ultrasonic homogenizer. The bacterial debris was removed by refrigerated centrifugation to give a crude enzyme solution. To the crude enzyme solution was added ammonium sulfate. Then, 30 to 60% of the precipitated fraction was desalted and passed through a DEAE Toyopearl column to collect a passed fraction. The fraction further underwent chromatography using phenyl Toyopearl and Q-sepharose to give a fraction exhibiting D-aminoacylase activity. The fraction was electrophoresed with sodium dodecylsulfate—polyacrylamide gel and a band was observed at about 56 kDa. The 56 kDa protein was sequenced for its N-terminal amino acid sequence, which was determined to be Thr-Asp-Ser-Thr-Arg- as shown in SEQ. ID. No. 3.

Example 5
Preparation of a Genomic DNA Library of Methylobacterium Mesophilicum MT 10894 (FERM P-17771)

The Methylobacterium mesophilicum was cultured for 2 days as described in Example 1. The bacterial cells were harvested by centrifugation and washed with a phosphate buffer (pH 7.8). From the bacterial cells, a genome DNA was prepared in accordance with a DNA separation procedure described in "Kiso Seikagaku Jikken Hou 2, Extraction, Separation and Purification, Koichi Anami et al., Maruzen Publication". The genome DNA thus prepared was completely digested with a restriction enzyme Sac I and fractionated by a DNA length by ultracentrifugation to collect DNAs with 3 kb or more. The DNAs were subject to DNA ligation with a vector pUC18 whose 5'-terminus had been dephosphorylated after digestion with the restriction enzyme SacI, to prepare a plasmid library. E. coli DH5α was transformed with the plasmid library. The transformant was applied on an LB (Luria-Bertani) agarose medium containing 50 μg/mL ampicillin and was statically cultured to form colonies.

Example 6
Activity Screening for the D-Aminoacylase From the Plasmid Library

Each colony formed in Example 5 was subject to liquid-phase shaking culture in an LB medium (1% bactotrypsin, 0.5% bactoyeast extract, 1% sodium chloride, pH 7.0) at 37° C. overnight. A transformant was precipitated by centrifugation and washed once with a 0.1 M phosphate buffer (pH 7.8). The bacterial cells were harvested by further centrifugation. The harvested bacterial cells were homogenized to give a crude enzyme solution. A transformant exhibiting D-aminoacylase activity whereby D-tryptophan is produced by a reaction with N-acetyl-D-tryptophan as a substrate was selected. The determination procedure will be described below.

Crude Enzyme Solution

The harvested bacterial cells were suspended in a 0.1 M phosphate buffer (pH 7.8) to a concentration of 0.1 mg/mL. After homogenizing the bacterial cells by an ultrasonic homogenizer, the debris was precipitated by a refrigerated centrifuge and the supernatant was collected as a crude enzyme solution.

Substrate Solution

A substrate solution was prepared by dissolving N-acetyl-D-tryptophan in a 0.1 M phosphate buffer (pH 7.8) to a concentration of 10 g/L.

Determination

To 200 μL of the substrate solution was added 200 μL of the crude enzyme solution. After reacting the solution at 30° C. for 1 hour, the reaction was quenched by adding 0.4 mL of a 1M phosphate buffer. After removing the debris by centrifugation, D-tryptophan produced in the reaction solution was determined by HPLC.

Example 7

Sequencing a DNA Encoding the D-Aminoacylase

A plasmid was extracted from the transformant exhibiting D-aminoacylase activity obtained in Example 6. Its physical map was prepared, which was as illustrated in FIG. 1. It was further sequenced. Sequencing was conducted by the Genetic Analyzer 310 (PE Applied Biosystem) using the BigDye Terminator Cycle Sequencing kit (PE Applied Biosystem). As a result, a base sequence of a DNA encoding a D-aminoacylase gene was obtained (SEQ. ID. No. 1). SEQ. ID. No. 2 shows a sequence after amino-acid translation of the base sequence of the D-aminoacylase. Its N-terminal amino acid sequence was in consistent with the results of N-terminal amino acid sequencing shown in Example 2. The molecular weight of the D-aminoacylase was estimated about 53 kDa from the amino acid sequence.

Example 8

Evaluation of a Reaction of N-Acetyl-DL-Tryptophan as a Substrate Using Transformed E. coli by the DNA Containing the D-Aminoacylase Gene Derived From Methylobacterium Mesophilicum MT 10894 (FERM P-17771) Preparation of a Bacterial Cell Suspension E. coli transformed by the plasmid shown in FIG. 1 in Example 7 was subject to shaking culture in an LB medium containing ampicillin (50 μg/mL) at 37° C. overnight. After culturing, the bacterial cells were harvested by centrifugation and washed with a 0.1 M phosphate buffer (pH 7.8). The bacterial cells were suspended in a 0.1 M phosphate buffer (pH 7.8).

Preparation of a Solution of N-acetyl-DL-tryptophan

A substrate solution was prepared by dissolving N-acetyl-D-tryptophan in a 0.1 M phosphate buffer (pH 7.8) to 200 g/L.

Determination

The above bacterial cell suspension (2.5 mL) and the substrate solution (2.5 mL) preheated at 40° C. were mixed and reacted at 40° C. (a reaction substrate concentration: 100 g/L). Twenty hours after the initiation of the reaction, a 100 μL aliquot of the reaction was taken and the reaction was quenched by adding the same amount of 1N NaOH. Then, the sample was diluted to 1/200 with an HPLC mobile phase and the bacterial cells were precipitated by centrifugation. The supernatant was analyzed by HPLC to determine concentrations of D- and L-tryptophans produced and of the substrate N-acetyl-DL-tryptophan. The results are shown in Table 4.

TABLE 4

| | |
|---|---|
| D-Tryptophan produced [mM] | 184 |
| L-Tryptophan produced [mM] | 0.0 |
| Remaining N-acetyl-DL-tryptophan [mM] | 218 |

TABLE 4-continued

| | |
|---|---|
| D-Tryptophan yield [%] | 45.8* |
| D-Tryptophan optical purity [% e.e.] | 100 |

*(D-Tryptophan produced [mM]) ÷ (D-Tryptophan produced [mM] + L-Tryptophan produced [mM] + Remaining N-acetyl-DL-tryptophan [mM]).

Example 9

Substrate Specificity of E. coli Transformed by the DNA Containing the D-aminoacylase Gene Derived from Methylobacterium Mesophilicum MT 10894 (FERM BP-7856) to an N-acetyl-DL-amino Acid Substrate specificity of E. coli transformed by the plasmid shown in FIG. 1 in Example 7 was compared for N-acetyl-DL-amino acids. In this example, the reaction was conducted at a substrate N-acetyl-DL-amino acid concentration of 5 g/L at 40° C. for 16 hours. Relative activities to a variety of N-acetyl-DL-amino acids together with optical purities and reaction yields were determined, assuming that D-aminoacylase activity was 100 when N-acetyl-DL-tryptophan was a substrate. The results are shown in Table 5.

TABLE 5

| Substrate | Relative activity (%) | Optical purity (% ee)/ D-Tryptophan yield (%)* |
|---|---|---|
| N-acetyl-DL-tryptophan | 100 | 100% ee/ 50% |
| N-acetyl-DL-5-hydroxytryptophan | 80 | 99% ee/ 48% |
| N-acetyl-DL-phenylalanine | 104 | 99% ee/ 50% |
| N-acetyl-DL-homophenylalanine | 45 | 100% ee/ 48% |
| N-acetyl-DL-4-fluorophenylalanine | 99 | 98% ee/ 50% |
| N-acetyl-DL-4-chlorophenylalanine | 89 | 98% ee/ 49% |
| N-acetyl-DL-tyrosine | 67 | 100% ee/ 48% |
| N-acetyl-DL-o-benzylserine | 30 | 100% ee/ 48% |

*(D-amino acid produced [mM]) ÷ (D-amino acid produced [mM] + L-amino acid produced [mM] + Remaining N-acetyl-amino acid [mM]).

INDUSTRIAL APPLICABILITY

Thus, this invention provides a novel D-aminoacylase derived from, e.g., Methylobacterium mesophilicum MT 10894 (FERM BP-7856) and a DNA encoding it. The D-aminoacylase of this invention is an industrially useful enzyme to allow a corresponding D-amino acid to be produced from an N-acylamino acid with a higher efficiency.

What is claimed is:

1. An isolated D-aminoacylase capable of catalyzing a reaction forming a D-amino acid by acting on the corresponding N-acyl-D-amino acid comprising the amino acid sequence of SEQ ID NO: 2.

2. The D-aminoacylase as claimed in claim 1, wherein said reaction takes place in an aqueous medium, wherein said reaction takes place in the presence of said D-aminoacylase, wherein said D-amino acid is D-tryptophan, and further wherein the rate of said reaction when the concentration of N-acetyl-D-tryptophan is 50 g/L is at least 40% of said reaction rate when the concentration of said N-acetyl-D-tryptophan is 5 g/L.

3. The D-aminoacylase as claimed in claim 1, wherein said reaction takes place in an aqueous medium, wherein said reaction takes place in the presence of said D-aminoacylase, wherein said D-amino acid is D-tryptophan, and further wherein the rate of said reaction when the concentration of N-acetyl-D-tryptophan is 100 g/L is at least 20% of said reaction rate when the concentration of said N-acetyl-D-tryptophan is 5 g/L.

4. A process for producing a D-amino acid comprising the step of forming said D-amino acid by the action of a D-aminoacylase on the corresponding N-acyl-D-amino acid, wherein said D-aminoacylase acts in an aqueous medium, and further wherein said D-aminoacylase comprises the amino acid sequence of SEQ ID NO: 2.

5. The process as claimed in claim 4, wherein said N-acyl-D-amino acid is N-acetyl-D-tryptophan, and further wherein said action of said D-aminoacylase occurs at a rate when the concentration of said N-acetyl-D-tryptophan is 50 g/L that is at least 40% of the rate when the concentration of said N-acetyl-D-tryptophan is 5 g/L.

6. The process as claimed in claim 4, wherein said N-acyl-D-amino acid is N-acetyl-D-tryptophan, and further wherein said action of said D-aminoacylase occurs at a rate when the concentration of said N-acetyl-D-tryptophan is 100 g/L that is at least 20% of the rate when the concentration of said N-acetyl-D-tryptophan is 5 g/L.

7. The process as claimed in claim 4, wherein said D-aminoacylase can be used directly from: (a) a culture obtained by culturing a transformant comprising the polynucleotide of SEQ ID NO: 1, or a variant thereof, wherein said variant encodes said D-aminoacylase comprising the amino acid sequence of SEQ ID NO: 2; (b) a transformant separated from the culture of (a); or (c) a processed material thereof.

8. The process as claimed in claim 4, wherein said aqueous medium contains said corresponding N-acyl-D-amino acid at a concentration of at least 50 g/L.

9. The process as claimed in claim 8, wherein said concentration is at least 100 g/L.

* * * * *